US00PP15193P2

(12) United States Plant Patent
Smith et al.

(10) Patent No.: US PP15,193 P2
(45) Date of Patent: Sep. 28, 2004

(54) ***MISCANTHUS* PLANT NAMED 'GOLD BAR'**

(50) Latin Name: *Miscanthus sinensis*
Varietal Denomination: Gold Bar

(76) Inventors: Michael Vern Smith, 20300 NW. Watson Rd., Scappoose, OR (US) 97056; Maurice Horn, 1818 SE. 47th, Portland, OR (US) 97215; Scott Christy, P.O. Box 478, Scappoose, OR (US) 97056

( * ) Notice: Subject to any disclaimer, the term of this patent is extended or adjusted under 35 U.S.C. 154(b) by 0 days.

(21) Appl. No.: 10/751,773

(22) Filed: Jan. 5, 2004

(51) Int. Cl.[7] ..... A01H 5/00
(52) U.S. Cl. ..... Plt./384
(58) Field of Search ..... Plt./384

*Primary Examiner*—Anne Marie Grunberg
*Assistant Examiner*—Annette H Para
(74) *Attorney, Agent, or Firm*—Penny J. Aguirre

(57) ABSTRACT

A new cultivar of *Miscanthus, Miscanthus sinensis* 'Gold Bar', that is characterized by its densely banded creamy yellow and green foliage, its short stature, its dense and upright plant habit, and its late season bloom.

1 Drawing Sheet

BACKGROUND OF THE INVENTION

The present invention relates to a new and distinct cultivar of *Miscanthus sinensis* and will be referred to hereafter by its cultivar name, 'Gold Bar'. 'Gold Bar' represents a new cultivar of Japanese silver grass, a cold hardy, perennial ornamental grass grown for landscape use.

The inventors discovered and selected the new cultivar, 'Gold Bar', in a cultivated area at their nursery in Scappoose, Oreg. 'Gold Bar' was discovered as a seedling produced by open-pollination of *Miscanthus sinensis* 'Strictus' (un-patented) and selected after evaluation in a test bed for a period of seven years.

The new cultivar 'Gold Bar' was selected for the unique banding pattern of its leaf blades combined with its dense, bushy and upright growth habit and its shorter height in comparison to 'Strictus' and other cultivars of *Miscanthus* known to the inventors.

Asexual reproduction of the new cultivar was first accomplished by culm division in Scappoose, Oreg. in late winter of 2000 by the inventors. The characteristics of this cultivar have been determined to be stable and are reproduced true to type in successive generations.

SUMMARY OF THE INVENTION

The following traits have been repeatedly observed and represent the characteristics of the new cultivar. The new *Miscanthus* has not been observed under all possible environmental conditions. The phenotype may vary somewhat with variations in temperature, day-length, light intensity, soil types, and water and fertility levels without, however, any variance in genotype. The measurements, observations, and descriptions that follow describe plants that were grown outdoors in Scappoose, Oreg. and observed for a period of seven years. These attributes in combination distinguish 'Gold Bar' from 'Strictus' and any other selections of *Miscanthus* known to the inventors.

1. The foliage of 'Gold Bar' exhibits a banding pattern of 12 to 17 creamy yellow bands while the banding pattern of 'Strictus' consists of 2 to 3 creamy yellow bands per leaf blade of about 10 inches in length.

2. 'Gold Bar' is short in stature; reaching a height of about 4 to 5 feet while 'Strictus' reaches a height of about 7 to 8 feet.
3. The growth habit of 'Gold Bar' is upright with rigid culms and foliage that is more dense and bushy in comparison to 'Strictus'.
4. 'Gold Bar' blooms in mid to late October in the Northwest and may not bloom in northern climates due to early frosts. 'Strictus' blooms in September.
5. 'Gold Bar' has more densely banded foliage, is more upright in habit, and has stiffer leaf blades than the *Miscanthus* cultivars 'Kirk Alexander' (un-patented) 'Puenktchen' (un-patented), and *Miscanthus* 'Little Zebra' (U.S. Plant Pat. No. 13,008), three cultivars known to the inventors to have banded foliage and short stature.

BRIEF DESCRIPTION OF THE DRAWING

The accompanying colored photographs illustrate the overall appearance and distinct characteristics of the new *Miscanthus.*

The photograph on the top of the sheet illustrates the overall habit and appearance of 'Gold Bar' in October in Scappoose, Oreg. as grown outdoors for seven years.

The photograph on the bottom of the sheet is of a plant as grown outdoors in a one-gallon container and is a close-up view of the banding pattern characteristic of the foliage of 'Gold Bar'. The colors in the photographs are as close as possible with the photographic and printing technology utilized. The color values cited in the detailed botanical description accurately describe the colors of the new *Miscanthus.*

DETAILED BOTANICAL DESCRIPTION

The following is a detailed description of the new cultivar as grown in an outdoor trial bed for seven years in Scappoose, Oreg. The color determinations are in accordance with The 2001 R.H.S. Colour Chart of The Royal Horticultural Society, London, England, except where general color terms of ordinary dictionary significance are used.

Botanical classification: 'Gold Bar' is a cultivar of *Miscanthus sinensis.*

Common Name: 'Gold Bar' Japanese silver grass or 'Gold Bar' Porcupine grass.

Parentage: Naturally occurring seedling by open-pollination of *Miscanthus sinensis* 'Strictus'.

General description:

*Blooming period.*—Blooms in mid to late October in the Northwest U.S. or not at all in shorter growing seasons or when early frosts occur. Blooms are retained over the winter if present.

*Plant habit.*—Herbaceous, clump-forming, ornamental grass with an upright, rigid form and dense, bushy foliage.

*Height and spread.*—Reaches up to 5 feet in height with a spread of about 18 inches (at base) in 4 years of growing time.

*Hardiness.*—Zone 4 to 9.

*Culture.*—Grows best in fertile, moist soil in full sun. Tolerates wet soils and light shade in climates with high temperatures.

*Diseases and pests.*—No susceptibility or resistance to diseases or pests that affect *Miscanthus* has been observed.

*Root description.*—Fibrous.

Growth and propagation:

*Propagation.*—Culm division, best divided in spring when in active growth.

*Time required for root development from a single division.*—A two to three culm division planted in a bark-based media will fully develop roots in a 6 inch deep 4 inch square container in 2 to 3 months when grown outdoors under standard summer temperatures and natural lighting in the Northwest U.S.

*Growth rate.*—Slow to moderate.

Culm (stem) description:

*General.*—Cylindrical, flattened, completely enclosed by leaf sheaths in a fan-like arrangement.

*Culm aspect.*—Rigid and held erect, none are cascading.

*Culm color.*—146B.

*Culm size.*—About ½ to ¾ inch wide, up to 4 to 5 feet in height on mature plants.

*Culm surface.*—Glabrous with very fine white hairs.

*Internode length.*—Varies from about 7 to 8 inches from the base of the culm to the first ligule and to about 1 to 3 inches for the more distal internodes. Internode length decreases gradually from the base to the apex of the culm.

*Ligule.*—Membranous, about ⅛ to 1/16" inches in width and 161B in color with very fine white hairs, encircles the entire culm.

Foliage description:

*Leaf shape.*—Linear.

*Leaf division.*—Simple.

*Leaf base.*—Sheathed.

*Leaf apex.*—Acute.

*Leaf aspect.*—Emerging leaves are erect, leaf blades diverge from leaf sheath at ligule at up to a 30° angle from center of culm. Blades are concave in respect to the culm.

*Leaf venation.*—Parallel, mid rib is raised on upper surface but not conspicuous, color matches the color of the leaf blades.

*Leaf margins.*—Entire, with sharp short bristles that are not visually noticeable.

*Leaf persistence.*—Foliage dries but is persistent throughout the winter.

*Leaf attachment.*—Sheathed. Leaf is sheathed from the base of culm and the blade extends out from the culm at a ligule.

*Leaf size.*—Up to about 12 inches in length, about ¼ inch in width tapering to a point at the apex.

*Leaf surface.*—Glabrous on upper and lower surface.

*Leaf number.*—About 23 to 27 per culm.

*Leaf arrangement.*—Alternate, 2 ranked.

*Leaf surface.*—Glabrous on upper and lower surface, bristles on margin.

*Leaf color and banding description.*—Banding is composed of alternating green and creamy yellow bands. Banding is typically limited to the leaf blade but occasionally banding occurs on the sheath. There are about 12 to 17 creamy yellow bands per leaf blade measuring 10 inches in length. Bands most frequently extend the entire width of the leaf blade and height of the bands range from ¼ inch to ½ inch. Creamy yellow coloration ranges from 10B to 10C, green bands are 137A in color. Banding pattern and colors on the lower surface match those of the upper surface.

Flower description:

*General description.*—Compact panicle, composed of numerous slender, pubescent racemes, cascading to one side, spikelets arranged in two equal pairs, 2 flowers per spikelet.

*Number of inflorescences.*—Typically only about 3 per plant (18 inches wide, 4 years old) and often they do mature in the growing conditions in the Northwest U.S.

*Lastingness of inflorescence.*—Panicles are persistent from fall through winter.

*Fragrance.*—None.

*Panicle size.*—Approximately 6 to 8 inches in length and 4 inches in width.

*Panicle color.*—Emerges a coppery red over white (effectively 178A, greyed red) and changes to a beige color during plant dormancy (effectively a color intermediate between 199D and 156A).

*Spikelet size.*—About ⅛ inch in length and 1/16 inch in width (excluding hairs).

*Spikelet hairs.*—Emerging from the base as a ring, long, up to ½ inch in length, very fine, 155D in color.

Reproductive organs:

*Androecium.*—Anthers; cigar-shaped, 1/16 inch in length, color is 187C, basofixed on very short filament. Pollen is moderate in quality, 14C in color, longitudinally dehiscence.

*Gynoecium.*—Pistil; 1, 2 plumose stigmas, stigma color is 187C. Ovary; 1-locular, superior, minute, not easily quantifiable in size and color.

*Caryopsis.*—Does not set viable seeds.

We claim:

1. A new and distinct cultivar of *Miscanthus* plant named 'Gold Bar' as herein illustrated and described.

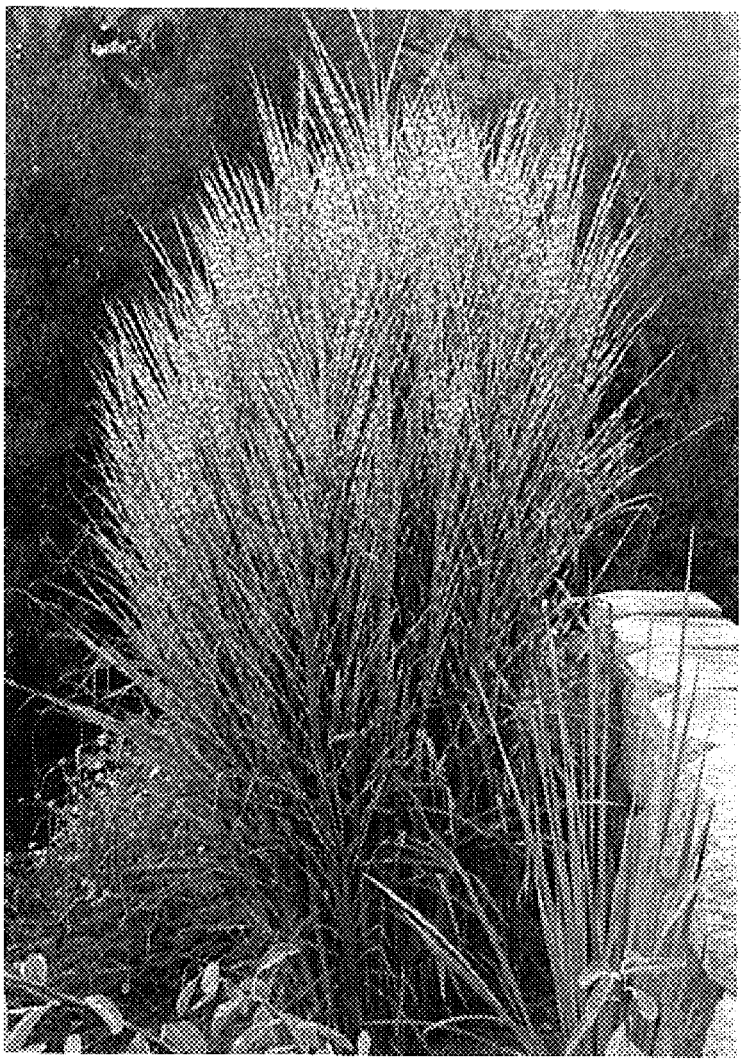
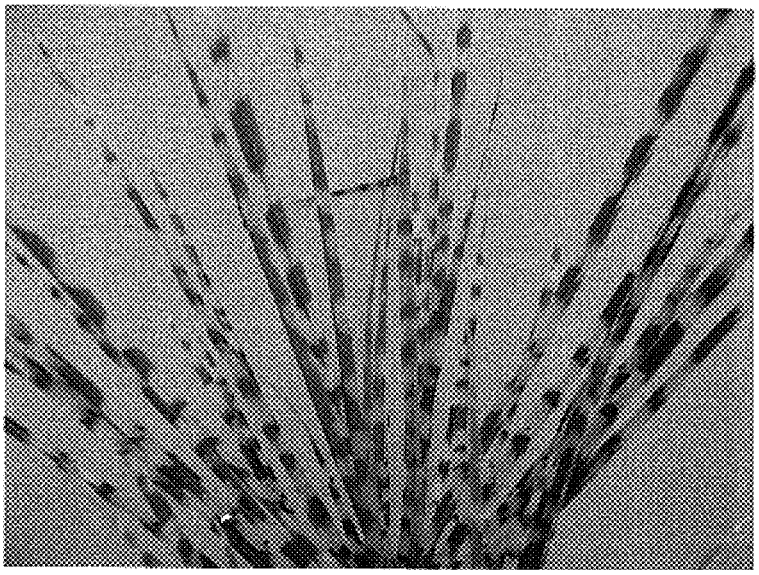

* * * * *